(12) United States Patent
Nilsson

(10) Patent No.: US 7,014,049 B2
(45) Date of Patent: Mar. 21, 2006

(54) DEVICE FOR BIO-AFFINITY MATERIAL

(75) Inventor: Kurt G. I. Nilsson, Lund (SE)

(73) Assignee: Glycorex Transplantation AB, Lund (SE)

( * ) Notice: Subject to any disclaimer, the term of this patent is extended or adjusted under 35 U.S.C. 154(b) by 69 days.

(21) Appl. No.: 10/114,314

(22) Filed: Apr. 3, 2002

(65) Prior Publication Data

US 2002/0146814 A1  Oct. 10, 2002

Related U.S. Application Data

(63) Continuation-in-part of application No. 09/091,486, filed on Jun. 19, 1998, now Pat. No. 6,444,655, and a continuation-in-part of application No. 09/722,241, filed on Nov. 27, 2000, now Pat. No. 6,686,457, and a continuation-in-part of application No. PCT/SE01/00241, filed on Feb. 2, 2001.

(51) Int. Cl.
*B01D 29/00* (2006.01)
(52) U.S. Cl. .............. 210/435; 210/445; 210/446; 210/450; 210/459; 210/500.21
(58) Field of Classification Search .......... 210/435, 210/445, 446, 450, 459, 500.21
See application file for complete search history.

(56) References Cited

U.S. PATENT DOCUMENTS

| | | | | |
|---|---|---|---|---|
| 4,468,324 A | * | 8/1984 | de Lappe et al. | 210/350 |
| 4,918,009 A | | 4/1990 | Nilsson | |
| 5,149,425 A | * | 9/1992 | Mazid | 210/198.2 |
| 5,246,840 A | | 9/1993 | Nilsson | |
| 5,372,937 A | | 12/1994 | Nilsson | |
| 5,405,752 A | | 4/1995 | Nilsson | |
| 5,667,676 A | * | 9/1997 | Alaska | 210/198.2 |
| 5,733,254 A | * | 3/1998 | Jones et al. | 604/6.04 |
| 6,444,655 B1 | * | 9/2002 | Nilsson | 514/61 |
| 6,653,109 B1 | | 11/2003 | Nilsson | |
| 6,686,457 B1 | * | 2/2004 | Nilsson | 536/4.1 |

FOREIGN PATENT DOCUMENTS

| | | | |
|---|---|---|---|
| WO | WO 93/03168 | | 2/1993 |
| WO | WO 94/29477 | | 12/1994 |
| WO | WO 97/23637 | * | 7/1997 |

\* cited by examiner

*Primary Examiner*—Francisco Prats
(74) *Attorney, Agent, or Firm*—Smith, Gambrell & Russell, LLP

(57) ABSTRACT

Bio-affinity material containing at least one biologically active saccharide which is covalently bound via at least one spacer to a cross-linked matrix and that the material is autoclaved. Apparatus for contacting body fluids with the bio-affinity material is disclosed.

28 Claims, 3 Drawing Sheets

DEVICE FOR BIO-AFFINITY MATERIAL

REFERENCE TO RELATED APPLICATIONS

The present application is a continuation-in-part of application Ser. No. 09/091,486 filed Jun. 19, 1998 now U.S. Pat No. 6,444,655 and application Ser. No. 09/722,241 filed Nov. 27, 2000 now U.S. Pat. No. 6,686,457 and application Ser. No. (PCT/SE01/00241) filed Feb. 2, 2001 which are relied on and incorporated herein by reference.

INTRODUCTION AND BACKGROUND

There is a need in the art for bio-affinity materials for the extra-corporal treatment of body fluids, especially blood or blood plasma of patients undergoing treatment for a variety of conditions, such as for example, kidney dialysis, and for a device for carrying out bio-affinity based treatments.

SUMMARY OF THE INVENTION

In one aspect of the present invention, there is described a material containing a so-called matrix, to which saccharide has been bound via a spacer as is further illustrated below. Another aspect of the invention describes a device for using the herein described bio-affinity materials for their intended purpose.

The active part of the bio-affinity material according to the invention, contains at least one saccharide part which has been bound via a spacer to a matrix according to the representation:

Saccharide-Spacer-Matrix

The matrix consists in general of a polymer, plastic, or a polysaccharide, and can bind a large number of saccharide-spacer units.

The term "saccharide" as used herein symbolizes a saccharide which has a biological or other affinity to another molecule, protein, virus or cell. Saccharide can consist of a glycoprotein, a neoglycoprotein, a glycopeptide or a glycosylated amino acid, a glycolipid, or a part, a fragment or a modified variant thereof, or another biologically active di- or trisaccharide or higher oligosaccharide substance.

A few non-limiting examples of biologically active saccharides, spacer and matrix which can be used according to the invention, are given below.

The active part of the material consists, as a non-limiting example, of either:

1. Blood group A—O($CH_2$)$_n$PhNH—CO—($CH_2$)$_m$NH—$CH_2$—CH(OH)—$CH_2$—O-matrix or:
2. Blood group B—O($CH_2$)$_n$PhNH—CO—($CH_2$)$_m$NH—$CH_2$—CH(OH)—$CH_2$—O-matrix where "matrix" denotes e.g. a polymer plastic or a polysaccharide, for example cross-linked agarose, specifically of the type Sepharose® Fast Flow, where —O($CH_2$)$_n$PhNH—CO—($CH_2$)$_m$NH—$CH_2$—CH(OH)—$CH_2$-is the spacer, according to the invention, to separate the saccharide, in the above examples blood group determinant A— and B—, respectively, from the matrix, where n and m, respectively, is an integer, n is for example one of 0, 1, 2, 3 or 4, and m is for example 1, 2, 3, 4, 5, 6 or 7, and where the linkage between —O— and matrix is formed between —O— and, for example, a carbon atom in the matrix.

Saccharide-spacer, for example Blood group A—O($CH_2$)$_n$ PhNH—CO—($CH_2$)$_m$NH— and Blood group B—O($CH_2$)$_n$ PhNH—CO—($CH_2$)$_m$NH—, respectively, is called the ligand herein. The matrix has a large number of bound molecules of ligand. Examples of bound amounts of ligand are 0.01, 0.1, 1, 2, 3, 4, 5, 6, 7, 8, 9, 10, 11, 12, 13, 14, 15, 16, 17, 18, 19, 20 mmole per liter of matrix, or an amount of mmole which is between two of the above given values per liter of matrix. Per liter matrix as used herein means the volume occupied by the ready-to-use matrix product.

A combination of two or more different saccharides can be used according to the invention, for example as non-limiting example, a combination of Blood group A—O($CH_2$)$_n$ PbNH—CO—($CH_2$)$_m$NH—, and Blood group B—O($CH_2$)$_n$ PhNH—CO—($CH_2$)$_m$NH—, where both ligands in this example are bound to matrix.

A feature of this invention is a device for using the bio-affinity materials described herein in the treatment of patients in need of such therapy, or for passage of blood, blood plasma, or other biological materials through the device. The bio-affinity material can, for this purpose, be filled into a column with in- and outlet passage through the column of, for example, blood plasma, or whole blood, from the patient.

The device is defined by a column filled with bio-affinity material. In a preferred embodiment, the device is autoclavable. Different types and different dimensions of column can be used. In general, the column can be built from a cylinder, two locking covers, and between each locking cover and the cylinder there is placed a porous membrane (or net). Each membrane is mounted between the locking cover and the cylinder with, for example, a silicon ring. Each locking cover has a centrally placed hole for passage of liquid, for example, blood or plasma or other biological fluids, through the column. Preferred examples are given in the drawings below.

BRIEF DESCRIPTION OF THE DRAWINGS

The present invention as it relates to the device will be further understood with reference to the drawings, wherein.

DETAILED DESCRIPTION OF INVENTION

The present invention will now be described in further detail.

Figure 1:
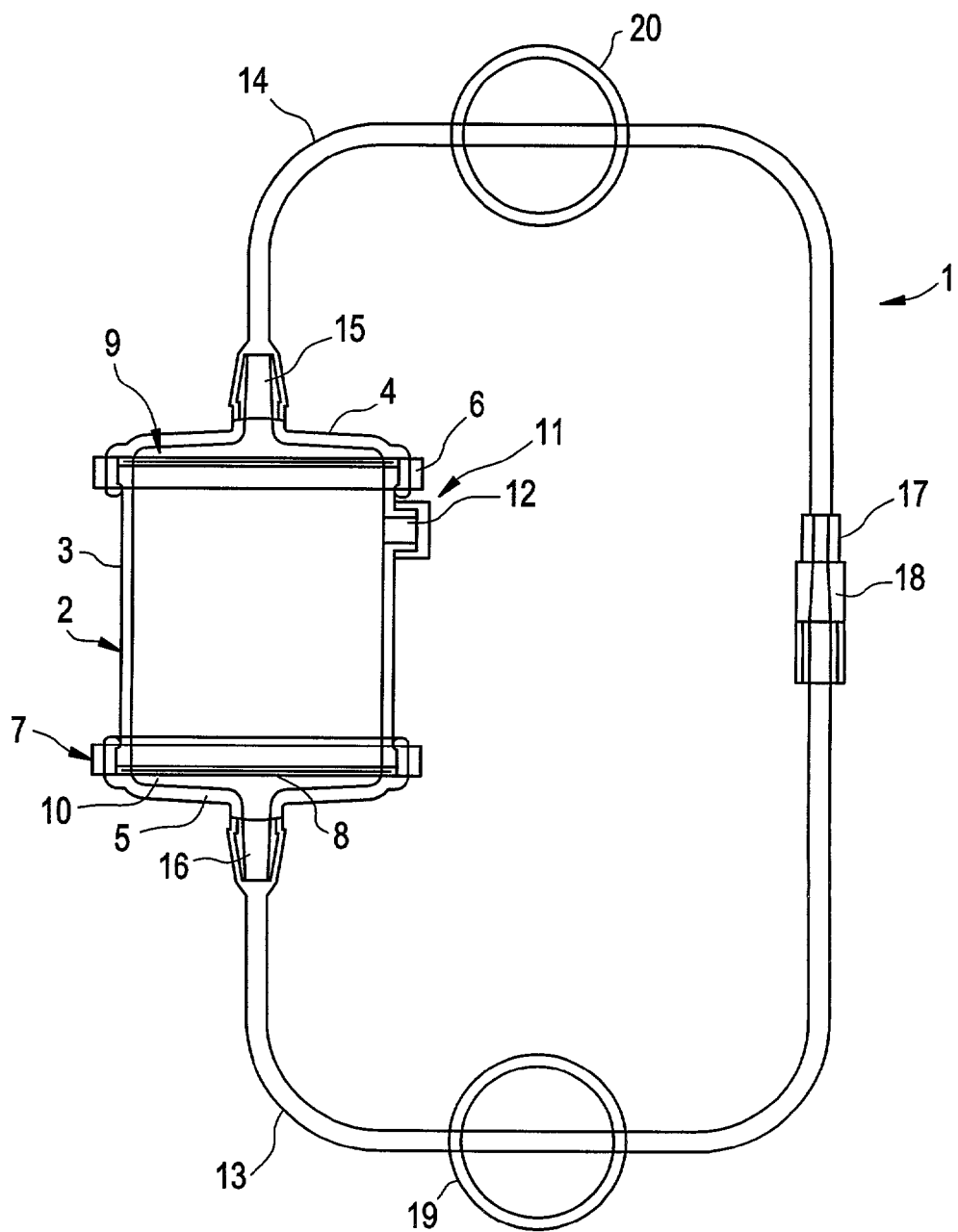
FIG. 1 is a schematic diagram of the device of the present invention.

Turning now to the drawings, FIG. 1 shows a schematic representation of the apparatus or device used to carry out the present invention involving contacting a body fluid such as plasma with the bio-affinity materials that are described herein. The device (1) includes an upright cylinder housing (2) formed by a circumferential vertical upstanding wall (3) fitted with a top locking cover (4) and a bottom locking cover (5). The function of the covers is to close the contents of the housing (2). An outer ring (6) is optionally located at the top of housing (2) and an outer ring (7) is optionally located at the bottom of housing (2) which seals the cylinder housing (2) at the top and bottom, respectively, by securing the top and bottom locking covers. A packing ring (8) and (9) is located at the bottom and top of the cylinder housing, respectively, and fits between the respective cover (4,5) and the housing (2). The packing ring is fitted with a retaining member which can be a mesh, member or net (10) having openings of such dimensions that it permits plasma to flow through the cylinder, but retains the bio-affinity material in said cylinder housing. The locking covers(4,5) are located at the top and bottom of the cylinder and function to secure the cylinder housing and make it tight to prevent loss of contents. A cap or "propp" (11) which is preferably a screw on cap is located to cover the port or opening (12) through which the material as described herein is filled. Tubing (13, 14) connects the system for providing circulation of the fluids. The locking covers (4, 5) are designed so as to form a tubular extension or projection (15,16) which enables an engaging relationship with tubing (13, 14). The projection extends at an angle of 90°0 from the plane of the locking cover. A male luer coupling (18) is shown in mating engagement with female luer coupling (17) which function to connect the ends of the tubing (13, 14) together. Valves (19) and (20) are located in the tubing lines (13, 14) for controlling or stopping the circulation of the fluid in the tubing. However, in operation each liner coupling would, when plasma treatment is desired, be connected to and used, for example, together with relevant contrifugation or plasma filtration equipment.

Figure 2:
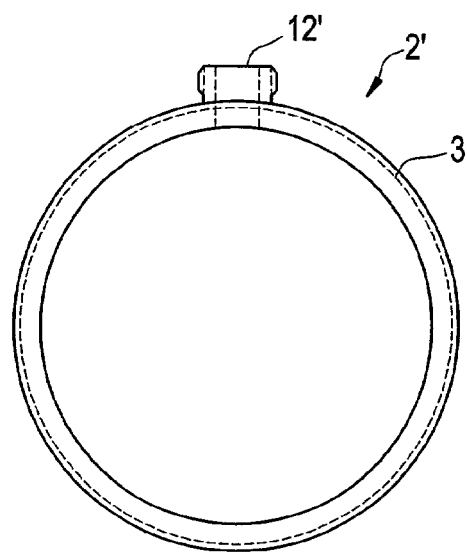
FIG. 2 is a schematic section view of a preferred example of the cylinder housing of the present invention.

FIG. 2 is a cross section view showing the cylinder housing (2) which is formed of a circular wall (3). Port 12 is shown in an open state.

Figure 3:
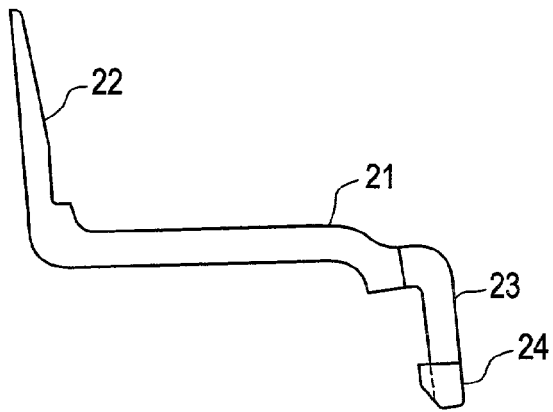
FIG. 3 is a partial side view of a preferred example of the locking mechanism used on the device of the present invention.

FIG. 3 is a cross section view and shows a portion of a locking cover which is used on the apparatus of the present invention to close the top and bottom of the cylinder housing (2). The locking covers consists of a circular disk-like portion (21) which has an upstanding section (22) located at angle of about 90° thereto; i.e. 90° to the plane of the disk (21). Another portion (23) of the locking cover is located on the periphery of disk body (21) and is also bent at an angle of approximately 90° terminating in a cap (24) with a projection thereon to hook onto the outside edge of the cylinder (2) housing.

Figure 4:
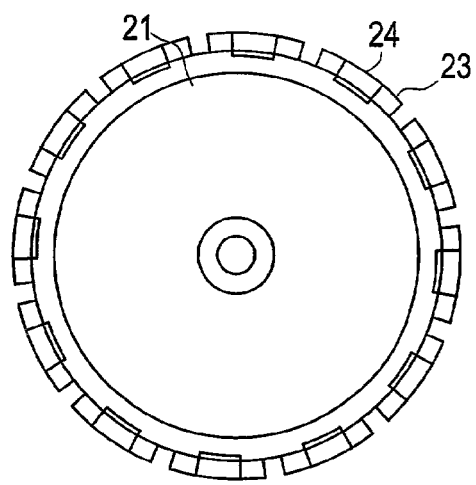
FIG. 4 is a schematic representation of the locking cover seen from below.

FIG. 4 is a bottom cross sectional view of the locking cover formed of the circular disk portion (21) and shows the depending portion (23) and the caps (24) with the projection to clip onto the terminal edge of the cylinder housing.

Figure 5:
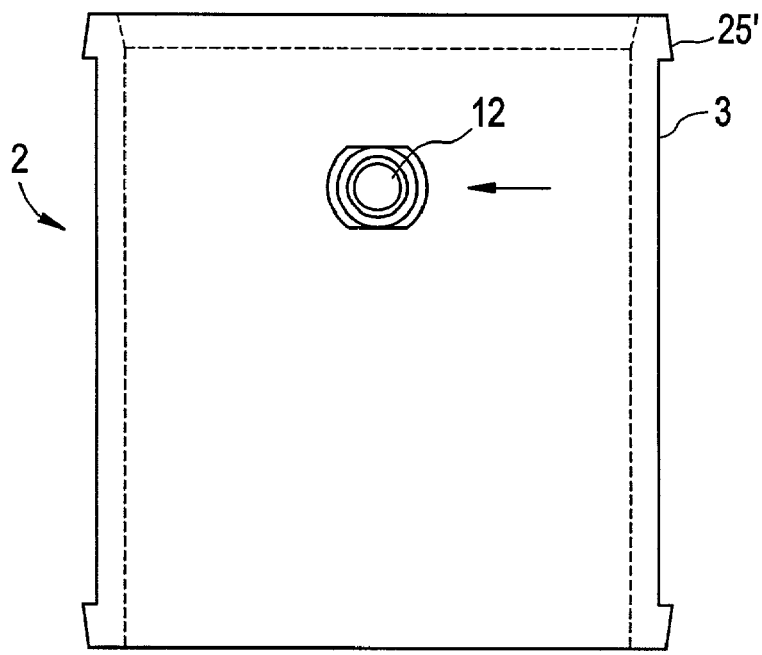
FIG. 5 is an elevational schematic view of the exterior cylinder housing of the present invention.

FIG. 5 shows cylinder housing (2) in an elevational view formed of the cylinder wall (3) having the open port (12) and terminal leading edges (25, 25') for engagement with the caps (24) of the locking cover.

Figure 6:
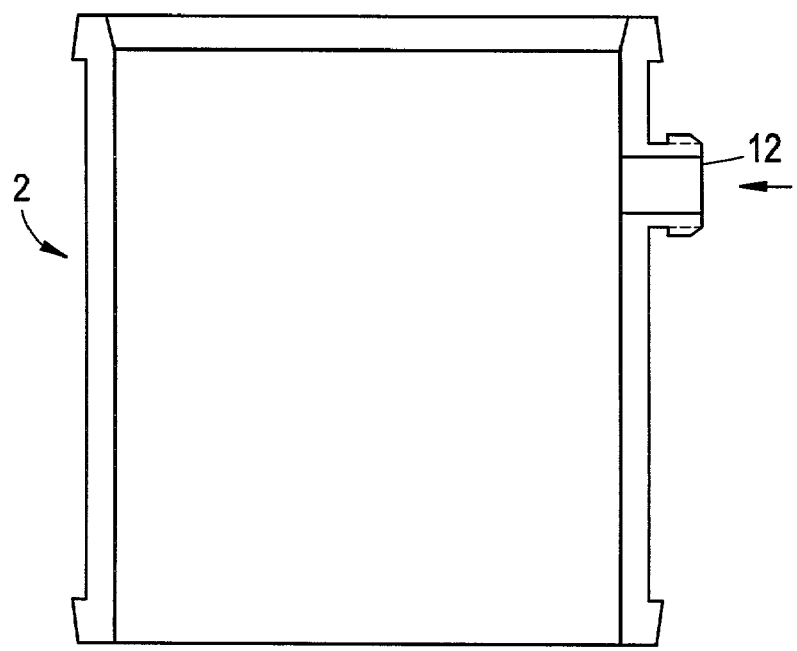
FIG. 6 is an elevational schematic side section view of the cylinder housing of the present invention.

FIG. 6 is a side sectional elevation view showing cylinder housing (2) and the open port (12) for filling the bio-affinity material into the cylinder housing (2).

A non-limiting example of a preferred bio-affinity material of the invention is:

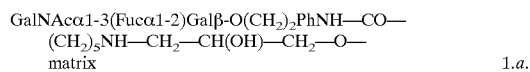
matrix                                             1.a.

This type of product can be produced by reaction between for example GalNAcα1-3(Fucα14 2)Galβ-O(CH$_2$)$_2$PhNH$_2$ and for example, a carbodiimide-activated, or an NHS-activated spacer-matrix, where matrix can be, for example, cross-linked agarose. A non-limiting example of NHS-activated spacer matrix is NHS-activated SepharoseR 4FF, where the latter is commercially available, or other cross-linked agarose or other matrix with corresponding properties. The reaction conditions can be chosen by the person skilled in the art and does not limit the scope of the invention. Other examples are product containing, bound in the same manner, a higher oligosaccharide than the A-trisaccharide in the above example, which contains the A-determinant terminally, for example A-determinant of type 1, 2, 3 or 4. The trisaccharide derivative GalNAcα1-3(Fucα1-2) Galβ-O(CH$_2$)$_2$PhNH$_2$ and other saccharide derivatives mentioned in this application can be produced with different chemical and/or biochemical methods and this does not limit the scope of the invention.

Further examples of product 1 above is a product where a combination of 1.a. above and one or more of mentioned blood group A variants, are bound via the same type of spacer as shown above to matrix, or via a different type of spacer.

A non-limiting example of a preferred variant of product 2 above which can be used to fill the device of this invention is:

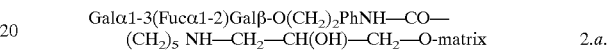
                                                                 2.a.

This type of product can be produced by reaction between for example Galα1-3(Fucα1-2 2)Galβ-O(CH$_2$)$_2$PhNH$_2$ and for example, a carbodiimide-activated, or an NHS-activated spacer-matrix, where matrix can be, for example, cross-linked agarose. A non-limiting example of NHS-activated spacer matrix is NHS-activated SepharoseR 4FF, where the latter is commercially available, or other cross-linked agarose or other matrix with corresponding properties. The reaction conditions can be chosen by the skilled person in the art and does not limit the scope of the invention. Other examples are product containing, bound in the same manner, a higher oligosaccharide, which contains the B-determinant terminally, for example B-determinant of type 1, 2, 3 or 4. Further examples of product 2 are material where a combination of 2.b. above and one or more of mentioned blood group B variants, are bound via the same type of spacer as above to matrix, or via a different type of spacer.

Instead of the —O(CH$_2$)$_2$PhNH— group in the formulas above, another suitable spacer or part of spacer can be used, as for example —O(CH$_2$)$_n$NH— or for example N(Ac)—(CH$_2$)$_n$NH—(Ac=acetyl group; n is an integer, for example 1, 2, 3, 4, 5, 6, or 7 or higher), or another aliphatic compound, or another aromatic compound.

The saccharide, for example the blood group A— or B-determinant, can also be bound, directly or indirectly, to an oligomeric substance acting as spacer, or part of spacer, as for example a mono-, di-, or higher oligosaccharide or polysaccharide, peptide, for example a peptide consisting of amide bound glycine and glutamic acid residues, for example Gly-(Glu-Gly)n-Glu, where n is an integer between for example 1 and 20. In this manner the saccharide-spacer consists of 1, 2, 3, 4, 5, 6, 7, 8, 9, or 10 or more saccharide units bound to each oligomeric substance or peptide.

The linkage between the saccharide and the peptide can for example be formed via O-glycosidically bound —O(CH$_2$)$_2$PhNH— group (see for example formulas 2.a. and 2.b. above), or via for example O-glycosidically bound —O(CH$_2$)$_n$NH—, (where n is an integer for example 1,2, 3,4,5,6,7 or higher), where NH— is bound via an amide linkage (NH—CO) to the carboxyl group on the side-chain of the Glu-residues in the peptide. —O in —O(CH$_2$)$_2$PhNH— and in —O(CH$_2$)$_n$NH—, respectively, is then bound glycosidically to the saccharide.

The peptide can first have been coupled to a matrix, for example, NHS-activated matrix, such as NHS-activated Sepharose® 4FF via the α-amino-group on the peptide, and thereafter the saccharide can be bound to the peptide via —O(CH$_2$)$_2$PhNH—, or for example —O(CH$_2$)$_n$NH—, to the carboxyl group on the Glu-residues in the peptide. This linkage between saccharide and Glu-residues can be achieved for example, by carbodiimide-(for example EDC-) mediated coupling, or by for example succinimide-mediated coupling. The saccharide-spacer can herewith be added to the reaction mixture in for example a desired molar excess in relation to the amount of moles of peptide, e.g. in a molar excess of 2, 3, 4, 5, 6, 7, 8, 9 or 10 times excess or more. These and other reaction conditions are chosen by the person skilled in the art and do not limit the scope of the invention. Non-limiting examples in this manner of bound amount of saccbarideis 0.01, 0.1, 1, 2, 3, 4, 5, 6, 7, 8, 9, 10, 11, 12, 13, 14, 15, 16, 17, 18, 19, 20 mmole of ligand per liter of matrix. Per liter of matrix here means the volume occupied by the ready to use matrix product.

Another example of a peptide is as above, but containing at least one lysine residue, where the ε-amino group in the lysine residue of the peptide is used for covalent coupling to matrix, for example NHS-activated matrix, such as NHS-activated Sepharose® 4FF, with subsequent coupling of, for example, saccharide-O(CH$_2$)$_2$PhNH—, or of for example saccharide-O(CH$_2$)$_n$NH—, to coupled peptide according to what has been describe above. Other linkages can be used according to the invention.

An advantage of using oligomeric ligands, as above mentioned examples of saccharide-peptide ligands, is that a stronger binding often can be achieved to that which is desired to be separated by the product, for example of antibodies towards blood group determinant or of other proteins, viruses or cells, and that therewith a more efficient product can be obtained as compared with non-oligomeric ligand.

As a non-limiting example of one preferred variant of material according to the invention and as a non-limiting example of its production there can be mentioned the coupling of about 3, 1.5 and 1 µmol, respectively, of the peptide Ac-Lys-(ε-amino)-Gly-Glu-Gly-Glu-Gly-Glu-Gly-Glu-Gly-Glu-Gly-Glu-Gly-amide via its ε-amino group, to 2 ml of NHS-activated matrix, such as, for example, NHS-activated Sepharose 4 FF, from Pharmacia-Biotech, at pH 7.5 (0.2 M sodium phosphate buffer +0.5 M NaCl) under 4 h at room temperature followed by 0.3 M Tris-HCl, pH 8, at room temp., over night. The gel is washed with Tris-buffer and 0.1. M MES, pH 4.7, which gave Peptide-Sepharose 4FF. Saccharide-spacer, as for example Galα1-3Galα-OPhNH$_2$, about 25 micromole, dissolved in 0.1 M MES-buffer, pH 4.7, was added to a solution of 48 mg EDC ((1-Ethyl-3-(3-Dimethylaminopropyl)-Carbodiimide)), to which was added 2 ml of Peptide-Sepharose 4FF, the mixture was incubated under 4 h at room temperature, after which it was washed with Tris-HCl, pH 8, 0.1 M acetate- and 0.1 M sodium phosphate buffer, respectively. The gels were tested for binding of antibodies, in the example of anti-Galα1-3Gal antibodies and showed a better binding of IgM antibodies as compared with the same amount of saccharide-spacer-Sepharose 4FF, obtained by coupling of the corresponding amount of Galα1-3Galα-OPhNH—, but without peptide, directly to NHS-activated Sepharose 4FF. Other saccharide derivatives than Galα1-3Galα-OPhNH$_2$ can be used according to the invention, such as for example Gal-NAcα1-3(Fucα1-2)Galβ-O(CH$_2$)$_2$PhNH$_2$ or Galα1-3 (Fucα1-2)Galβ-O(CH$_2$)$_2$PhNH$_2$.

The saccharide-peptide conjugate can for example first be prepared by using the ε-BOC-derivative (BOC=tert-butyloxycarbonyl group), situated on the ε-amino group of the lysine residue of the peptide in the above mentioned example. The saccharide-spacer-peptide conjugate is then first formed by for example EDC-mediated reaction between amino groups on the saccharide-spacer and the carboxyl groups on the peptide, the resulting conjugate can be purified by, for example, Sephadex chromatography, the BOC group can be eliminated, by for example, trifluoroacetic acid reaction according to standard conditions for peptide chemistry, and the conjugate can be coupled, for example, in the same manner as describe above via the ε-amino group of the lysine residue to the matrix, for example, a carbodiimide-activated, or an NHS-activated spacer-matrix, where matrix can be, for example, cross-linkagarose. A non-limiting example of NHS-activated spacer-matrix is NHS-activated SepharoseR 4FF, where the latter is commercially available, or other cross-linked agarose or other matrix with corresponding properties.

As another non-limiting example of peptide there can be mentioned peptide consisting of amide bound Gly and Lys units, for example Gly-(Lys-Gly)n-Gly, where n is an integer between for example 1 and 20. In this case for example the peptide can be bound to the saccharide via amino groups on the peptide, a N-glycosidic linkage is formed between the reducing end on the saccharide and the ε-amino group on the lysine residue(s), and the saccharide-peptide can be coupled to the matrix via, for example, either the remaining amino group(s) on the peptide to for example NHS-activated Sepharose as described above, or via, for example, the terminal COO-group on the peptide and amino groups on amino group containing matrix, for example aminohexyl-Sepharose (by for example carbodiimide or succinimide coupling according to examples given above). The N-glycosidic linkage can be stabilized by acetylation under standard conditions, for example before coupling to the matrix, e.g. NHS-activated Sepharose 4FF. In the same manner as for the Gly-Glu-peptide above also an aliphatic or aromatic spacer can be used to bind the saccharide to the lysine residues of the peptide, but in this case is, for example, glycosidically bound groups of the type —O(CH$_2$)$_2$Ph-COO—, or for example —O(CH$_2$)$_n$COO—, are used for carbodiimide- or succinimi-mediated coupling between saccharide and lysine residues in the peptide.

The coupling to the peptide can also be carried out by first coupling the saccharide part to the amino acid and thereafter form the peptide linkages.

Further examples of ligands according to the invention, is to use a protein or a polysaccharide as spacer, or part of the spacer, between saccharide and matrix. Here for example a protein, such as serum albumin, or a polysaccharide, such as dextran, is used. The saccharide can then first be coupled to the protein, or to the polysaccharide, which then is coupled to the matrix. The same type of chemistry as exemplified above can, as non-limiting examples, be used to achieve the linkages between saccharide, protein, or polysaccharide, and matrix. This does not limit the scope of the invention, and the conditions are chosen by the expert.

To use a peptide, protein or polysaccharide according to what have exemplified above, can in some cases be an advantage to increase the ability of the material to bind protein, and thereby increase the efficiency of the product according to the invention.

As another example of matrix there can be mentioned the filters which are used for plasma separation. These can be chemically modified with standard technique and be used for coupling of oligomeric ligand or of non-oligomeric ligand mentioned in this description. In this manner product is achieved which can be used for specific removal of proteins in connection with blood plasma separation, for example antibodies directed towards Galα1-3Gal and other so called xeno antigens in connection with xenotransplantation.

In a variant of the invention, the product in addition contains a Tris structure according to the following non-limiting example:

(HOCH$_2$)$_3$C—NH—CO—(CH$_2$)$_5$NH—CH$_2$—CH(OH)—CH$_2$—O-matrix where (HOCH$_2$)$_3$C—NH—is a so called Tris-group. This product can be made by reaction between Tris-HCl and for example, NHS-activated spacer-matrix, where matrix can be cross-linked agarose. A non-limiting example of NHS-activated spacer-matrix is NHS-activated SepharoseR 4FF.

In the production of the product according to the invention there can be used, for example, commercially available activated matrix, for example so called NHS-activated Sepharose®4 Fast Flow (NHS—is an abbreviation of N-hydroxysuccinimide; this variant of agarose is relatively strongly cross-linked, commercially available), which is present in the form of practically spherical particles. The particle size is chosen in, for example, the interval 45–165 µm. This activated matrix can be used for covalent binding of for example, Blood group A—O(CH$_2$)$_n$PhNH$_2$—, to give product 1.a. above, and of Blood group B—O(CH$_2$)$_n$PhNH$_2$, which give product 2.b. above, respectively, at, as non-limiting and typical examples, pH 7.5 or pH 8.0, in buffer, for example 0.1 M sodium phosphate as non-limiting example, under for example 1, or 2 hours or for 20 hours, and in the example at room temperature. After the reaction, the material is washed for example on a glass filter or under other conditions, for example sterile conditions, with, for example, buffer and is subsequently treated with for example Tris-HCl buffer to react any remaining reactive groups. The person skilled in the art will be able to choose the conditions for the reactions and this does not limit the scope of the invention. See also the above given example in connection with the preparation of Galα1-2 3Gal-Peptide-Sepharose 4FF.

In the production of the product according to the invention there can, as another example, be used the so-called epoxy-activated Sepharose® 4 Fast Flow, to which is covalently bound, for example Blood group A—O(CH$_2$)$_n$PhNH—CO—(CH$_2$)$_m$NH—, or to which is covalently bound Blood group B—O(CH$_2$)$_n$PhNH—CO—(CH$_2$)$_m$NH—, where n or m are specified above as are Blood group A and Blood group B, respectively.

As has been mentioned above, a combination of ligands can also be covalently bound to the matrix.

The products can be used, for example, for extra-corporal removal of blood group A— and blood group B-antibodies, respectively, e.g. for purification of blood, or for example, before a transplantation, for example over the blood group barrier. The product can be used in general for different types of transplantation as a part of the treatment of the recipient before and during, and eventually after the transplantation. Lowering of anti-A and/or anti-B antibody titers have been shown in several studies to facilitate cross-ABO transplantation. Thus, anti-A antibodies of a blood group 0, or a blood group B patient are lowered or removed before transplantation of a blood group A organ, by extra-corporal treatment as described above of the blood or blood plasma of the patient, with the device according to the invention containing blood group A. Moreover, anti-B antibodies of a blood group 0, or a blood group A patient can be lowered or removed before transplantation of a blood group B organ, by extra-corporal treatment as described above of the blood or blood plasma of the patient, with the device according to the invention containing blood group B. This to be able to solve the problem of blood group incompatibility between donor and recipient. The bio-affinity material can for this purpose be filled into a column housing with in- and outlet for passage through the column of for example blood plasma, or whole blood, from the patient who shall be transplanted or who is undergoing a transplantation procedure. The use of the product is therefore not restricted to for example, blood group incompatible transplantation, but can also be used, for example, for blood group compatible transplantation, to minimize problems in connection with donor and recipient of the same blood group, but of different blood group subgroups, for example A1, A2 etc.

Other non-limiting examples of saccharide according to the specific examples 1 or 2 above, are structures where the saccharide part consists of Galα1-3Galα-, Galα1-3Galβ, Galα1-3Galβ1-4Glcβ-, Galα1-3Galβ1-4GlcNAcβ-, Galα1-2 3Galβ1-4GlcNAcβ1-3Galβ1-4Glcβ-, or of oligomeric ligands, such as for example (Galα1-3Galα-)n-, (Galα1-3Galβ-)n-, (Galα1-3Galβ1-4Glcβ-)n-, (Galα1-3Galβ1-4GlcNAcβ-)n-, (Galα1-3Galβ1-4GlcNAcβ1-3Galβ1-4Glcβ-)n-, or (Galα1-3Galα-spacer)n-, (Galα1-3Galβ-spacer)n-, Galα1-3Galβ1-4Glcβ-spacer)n-, (Galα1-3Galβ1-4GlcNAcβ-spacer)n-, (Galα1-3Galβ1-4GlcNAcβ1-3Galβ1-4Glcβ-spacer)n-, where n is an integer larger than 1. As mentioned above for other saccharides, different spacers can be used in connection with above mentioned saccharides. Non-limiting examples of the spacer have been given above, for example of non-oligomeric, oligomeric, and of polymeric type, respectively.

These structures can be of interest to be used in for example a column or in a plasmafilter, for example before and after xenotransplantation to reduce so called xeno-antibodies from the patient's blood (whole blood column) or plasma.

Other carbohydrate structures active towards other antibodies, for example antibodies against cancer-antigens, for example prostate-, breast-, intestine-, or skin cancer, can be used to form product according to the invention. This can be of interest for example to isolate antibodies from blood or plasma against said antigen and after elution from the product, be used for treatment of said cancer diseases, or to produce reagents, or for example, to remove an excess of antibody derivatives from blood or plasma in immunotherapy of cancer. Other carbohydrate structures specific for e.g. toxins, virus and/or bacteria, can also be used to form product according to the invention. These products can be used to, for example, purify or eliminate virus and/or bacteria from e.g. whole blood or plasma or from other materials, for example food products or from water.

A combination of two or more different ligands (Saccharide-spacer) bound to matrix, can be used in the product according to the invention. The saccharides can then be different, and/or the spacer can be different.

The product according to the invention, allows for example a combination of high flow rate (for example in the interval 20–60 ml/min), minimal drop in pressure over the column, and a good binding capacity also of molecularly larger proteins, for example antibodies, such as IgG and IgM. As a non-limiting example there can be mentioned a single passage of more than one liter blood group B plasma with a flow rate of about 40 ml/minute through a column with about 3 micromol of blood group A trisaccharide per ml Sepharose 4 FF, and with a total product volume of 62 ml, and an average particle size of 90 µm, practically eliminated all antibodies reactive against blood group A. Similar result was obtained with blood group B product. The products were built according to 1.a. and 2.b. above from A— and B-trisaccharide-spacer and NHS-activated Sepharose$^R$ 4 Fast Flow.

One or more of the devices according to the invention can be used in parallel or one device coupled after the other. Thus, for example, one device containing bio-affinity material with blood group A and one device containing bio-affinity material with blood group B can be used in parallel or in sequence to remove both anti-A and anti-B antibodies from blood or blood plasma, thus creating, for example, universal plasma which can be given to patients irrespective of blood group of the patient. The column volume is chosen for the purpose and can be for example of a size of, for example, 10 ml, 20 ml, 40 ml, 60 ml up to a size of for example 500 ml or higher depending on which volumes are desired to process. The column volume can be for example of a value between the given values. Different types of column housing of different dimensions can be used. The bio-affinity material according to the invention functions, as non-limiting example, in the type of column housing with the dimensions used for the product ImmunoSorba®, (which has protein A as ligand bound to matrix), which has an inner volume between the porous membranes of about 62 ml (that is allows filling of 62 ml material according to the invention).

When using products according to the invention for treatment of plasma, in general there can be used membranes which have a lower porosity and matrix particles which have lower particle size as compared with the case when the product is applied for treatment of whole blood. Thus, for example, in the case of the treatment of plasma, membrane with porosity of for example 30 micrometer, thus retaining particles of diameter larger than 30 μm, or membranes with a porosity in the range 20 to 40 micrometer, and particle size of matrix of for example 90 micrometer, or matrix of for example particle size in the range 40–200 micrometer, can be used. When using products according to the invention for treatment of whole blood, membranes with porosity of for example 30 micrometer or 70 micrometer, or membrane with a porosity in the range 20 to 100 micrometer, can be used, and the particle size of the matrix can be for example 150 micrometer, or the matrix particle size can be for example in the interval 100–250 micrometer. The porosity is chosen by the person skilled in the art and does not limit the scope of the invention.

The filling of the bio-affinity material according to the invention into the column can be done using different principal methods. According to the invention, the bio-affinity material can for example either be autoclaved first and thereafter be filled aseptically in the column, or the bio-affinity material can, as an example of another preferred form of the invention, first be filled in the column and thereafter the column with the bio-affinity material is autoclaved.

Non-limiting example of autoclaving is treatment in an autoclave of for example counter-pressure type, which involves treatment under at least 20 minutes at 121° C. or higher and with for example water steam. Other conditions can be chosen by the person skilled in the art from what is suitable, e.g. sterility and stability of the product. As an example there can be mentioned that the Saccharide-spacer-Matrix according to examples 1.a. and 2.b., obtained via coupling of the respective ligand to NHS-activated Sepharose 4FF, exhibits the same properties after autoclaving as before autoclaving concerning tested parameters such as antibody binding properties and other properties.

The column either completely, or partially, filled with material according to the invention, can for example be constructed in materials which allows for autoclaving (biocompatible plastic materials which can be autoclaved are commercially available, e.g. column housing and locking covers are made of special polycarbonate, tubings of PVC or silicon material and rings of silicon) and/or for example to allow aseptic packing of material according to the invention. Column housings exists on the market for extracorporal blood treatment, e.g. Immunosorba. This allows for aseptic filling, but not for autoclaving.

Non-limiting example of autoclavable column housings as illustrated in one embodiment thereof in FIG. 1 include a column housing (2) built from autoclavable materials. The column housing typically has two locking covers (4,5). Between each locking cover and cylinder and before placement of the locking covers (4, 5) onto the cylinder, there is placed a porous membrane (9, 10) (that is two membranes and rings for each column), which allows for passage of plasma or whole blood but not for passage of the bio-affinity material according to invention. Each membrane is mounted between the locking cover and the cylinder with for example a silicon ring with a fitting groove of the same or about the same diameter as the cylinder. Every silicon ring has for example a grove which allows for fitting the circular membrane in the groove in the silicon ring. The membrane is mounted in the silicon ring and is placed between the locking cover and the ending of the cylinder housing, after which each locking cover is fitted onto the cylinder. The silicon ring with the membrane therewith is enclosed between the locking cover and the cylinder ending. The same procedure is carried out for the other ending of the cylinder. Each locking cover has a centrally placed hole with a projection (15, 16) which allows for connecting a biocompatible and autoclavable set of tubings (13, 14) equipped with connections (17, 18) of e.g. the luer type for connection of other equipment used in extracorporal treatment.

It is preferred that the locking covers and the cylinder are connected with a clip mechanism where for example the locking covers are equipped with one or more clips (for example in each one of the locks there are 2, 3, 4, 5, 6, 7, 8, 9, 10, 11, 12, 13, 14, or more separate clips which are situated beside each other with a defined interspace), and the cylinder has on its outer side one or more protruding edge(s) placed at a distance, e.g. of 2, 3, 4, 5, or 6 mm from the top and from the bottom, respectively, of the cylinder. The clips can be protruding down from the locking covers and can for example be homogeneous, or each one be equipped with a cavity to allow for a larger flexibility without being broken. In this manner the silicon ring with the membrane according to the above can be placed between the locking cover and the respective cylinder ending, and the locking cover is thereafter pressed onto the cylinder, whereupon the clips are pressed under the protruding edges on the cylinder and stays there, and the silicon ring with the porous membrane is consequently sealed between the locking cover and the cylinder housing.

Alternatively the locking covers and the top and bottom edges of cylinder housing (2) can be equipped with matching screw threads.

In order to fill the so mounted column housing with material according to the invention, the cylinder part can be equipped with a circular opening (12) with a protruding part, which has threads, on the outer wall of the cylinder to allow for connection of tubing used for filling of the material. After filling of the material into the column housing, a biocompatible plug (11) with threads which matches the threads of the protruding part on the cylinder, is mounted. In the center of the plug is a protruding tap which fits into the circular hole of the cylinder and which has a length which corresponds to the height of the protruding part. In this manner an almost flat surface is achieved inside the cylinder at the circular opening.

For the autoclaving of a column filled with bio-affinity material according to the invention and connected with a set of tubings, an outer ring of e.g. PVC material, and with an inner diameter which corresponds with the outer diameter of the column, can be mounted around the each locking cover before the autoclaving. This can be done in order to minimize any deformation of the cylinder under the autoclaving process. This principle has been successfully used under autoclaving of column filled with material according to the above.

All mentioned components of the column house in a preferred example according to the invention with autoclavable column house, are autoclavable and biocompatible. Locking cover, membrane, cylinder, plug, and tubing with luer coupling can be made of biocompatible plastic material. For example, in the preferred embodiments, the cylinder and locking covers can be fabricated from polycarbonate, the ring of silicon rubber, the membrane net of polyester, tubing and luer couplings of PVC and the plug of acrylobuta dienestyrene which are all bio-compatible.

Column housing completely or partially filled with bio-affinity material according to the invention and equipped with above mentioned closed tubing set and plug can be autoclaved. According to the invention this facilitates the achievement of sterility of the flow path of the products. With earlier methods sterile (aseptic) fillings have been carried out, but are difficult to achieve.

What is claimed is:

1. An apparatus containing at least one biologically active saccharide covalently bound by at least one spacer to a cross linked matrix material, said apparatus being autoclavable and comprising:
    a cylindrical container defined by a circumferential wall, having a top end and a bottom end, each of said top end and said bottom end having a protruding edge,
    a port defining an opening in said circumferential wall, said port protruding from the circumferential wall in an outward direction,
    a top lock cover in the form of a circular disk which has a plurality of downward projections to clip on to and under the protruding edge of said cylindrical container, said top lock cover being attachable to the top end of said container, said top lock cover having a central opening,
    a bottom lock cover in the form of a circular disk which has a plurality of upward projections to clip onto and over the protruding edge of said cylindrical container, said bottom lock cover being attachable to the bottom end of said container with said bottom lock cover having a central opening,
    said downward projections being of sufficient flexibility to engage with the protruding edge of said container and to permit said top lock cover to be pressed onto the container,
    optionally an outer ring located outside and adjacent to the top and bottom of the cylindrical housing to engage with and secure the top lock cover and bottom lock cover, respectively,
    a cover for said port,
    a first packing ring positioned between the upper end of said container and said top lock cover,
    a second packing ring positioned between the bottom end of said container and said bottom lock cover,
    said first and second packing ring each being fitted with a membrane located adjacent each of the top end and the bottom end of said container.

2. The apparatus according to claim 1 wherein the saccharide is for treating blood plasma, or whole blood.

3. The apparatus according to claim 1 that it has been autoclaved.

4. The apparatus according to claim 1 wherein each said membrane is porous for passage of liquid but which can retain a material represented by saccharide-spacer-matrix.

5. The apparatus according to claim 1 formed of biocompatible materials.

6. The apparatus according to claim 1 where each membrane has a porosity of in the range of 20 to 100 micrometer.

7. The apparatus according to claim 1 wherein the membrane has a porosity capable of retaining particles with a mean particle size of 40–250 micrometer.

8. The apparatus according to claim 1 where said container has an inner volume in the range of 10 ml to of 500 ml.

9. The apparatus according to claim 1 further comprising a tubing connected to each of the lock covers and two luer couplings for connecting said tubing.

10. The apparatus according to claim 9 where the tubing and luer couplings are biocompatible.

11. The apparatus according to claim 1 where each lock cover has a plurality of clips, which are situated beside each other with a defined interspace, the container having on its outer side a protruding edge near the top and the bottom, respectively, of the container, said clips protruding down from the lock cover and of sufficient flexibility to engage with the protruding edge of the container, and to permit the lock covers to be pressed on the container, whereupon the clips are pressed under the protruding edges on each lock cover.

12. The apparatus according to claim 1 wherein the outer ring at the top and bottom is of plastic and have an inner diameter which corresponds with the outer diameter of each lock cover.

13. The apparatus according to claim 1 where the column housing and lock covers are made of biocompatible polycarbonate, tubings are PVC or silicon polymer.

14. The apparatus according to claim 1 which has been autoclaved.

15. The apparatus according to claim 14 which has been autoclaved using steam.

16. The apparatus according to claim 14 which has been autoclaved for at least 20 minutes, and at a temperature of at least 120° C.

17. The apparatus according to claim 1 completely or partially filled with or equipped with closed tubing set and plug, which has been autoclaved.

18. An apparatus containing a material which is at least one biologically active saccharide covalently bound by at least one spacer to a cross linked matrix, said apparatus being autoclavable and comprising:
    a cylindrical container defined by a circumferential wall, having a top end and a bottom end, each of said top end and said bottom end having a protruding edge,
    a port defining an opening in said circumferential wall, said port protruding from the circumferential wall in an outward direction, a top lock cover in the form of a circular disk which has a plurality of projections to clip on to the protruding edge of said cylindrical container, said top lock cover being attachable to the top end of said container, said top lock cover having a central opening, a bottom lock cover in the form of a circular disk which has a plurality of projections to clip on to the protruding edge of said cylindrical container, said bottom lock cover being attachable to the bottom end of said container with said bottom lock cover having a central opening, said projections being of sufficient flexibility to engage with the protruding edge of said container and to permit said top and bottom lock cover to be pressed onto the container, optionally an upper outer ring fitted over a peripheral portion of said top lock cover to secure said top lock cover to said container, optionally a lower outer ring fitted over a peripheral portion of said bottom lock cover to secure said bottom lock cover to said container, a cover for said port, a first packing ring positioned between the upper end of said container and said top lock cover, a second packing ring positioned between the bottom end of said container and said bottom lock cover, a membrane located adjacent each of the top end and the bottom end of said container.

19. A method for filling the apparatus according to claim 1 comprising introducing said saccharide into the cylinder housing by connecting the cylinder housing with tubing used for filing of the saccharide, said cylinder housing having housing having an opening in a wall thereof, after filling of the saccharide into the column housing through said opening, mounting a bio-compatible plug with threads which match threads of a protruding part of said opening on the cylinder onto said opening.

20. A method for filling the apparatus according to claim 18 comprising introducing said saccharide into the cylinder housing by connecting the cylinder housing with tubing used for filing of the saccharide, said cylinder housing having housing having an opening in a wall thereof, after filling of the saccharide into the column housing through said opening, mounting a bio-compatible plug with threads which match threads of a protruding part of said opening on the cylinder onto said opening.

21. The apparatus according to claim 1 filled with a saccharide for filtering blood plasma, or whole blood.

22. The apparatus according to claim 1, wherein said apparatus contains a bio-affinity material consisting of Blood group A—O(CH$_2$)$_n$PhNH—CO—(CH$_2$)$_m$NH—CH$_2$—CH(OH)—CH$_2$—O-Matrix or of Blood group B—O(CH$_2$)$_n$PhNH—CO—(CH$_2$)$_m$NH—CH$_2$—CH(OH)—CH$_2$—O-Matrix where n and m, respectively, is an integer, n is 0, 1, 2, 3 or 4, and m is 1, 2, 3, 4, 5, 6 or 7, and where the linkage between —O— and Matrix is formed between —O— and a carbon atom in the Matrix, for removal of blood group A— or of blood group B-antibodies, respectively, from blood or plasma.

23. The apparatus according to claim 18, wherein said apparatus contains bio-affinity material consisting of Blood group A—O(CH$_2$)$_n$PhNH—CO—(CH$_2$)$_m$NH—CH$_2$—CH(OH)—CH$_2$—O-Matrix or of Blood group B—O(CH$_2$)$_n$PhNH—CO—(CH$_2$)$_m$NH—CH$_2$—CH(OH)—CH$_2$—O-Matrix where n and m, respectively, is an integer, n is 0, 1, 2, 3 or 4, and m is 1, 2, 3, 4, 5, 6 or 7, and where the linkage between —O— and Matrix is formed between —O— and a carbon atom in the Matrix, for removal of blood group A— or of blood group B-antibodies, respectively, from blood or plasma.

24. The apparatus according to claim 1 wherein said apparatus contains bio-affinity material consisting of Blood group A—O(CH$_2$)$_n$PhNH—CO—(CH$_2$)$_m$NH—CH$_2$—CH(OH)—CH$_2$—O-Matrix and of Blood group B—O(CH$_2$)$_n$PhNH—CO—(CH$_2$)$_m$NH—CH$_2$—CH(OH)—CH$_2$—O-Matrix where n and m, respectively, is an integer, n is 0, 1, 2, 3 or 4, and m is 1, 2, 3, 4, 5, 6 or 7, and where the linkage between —O— and Matrix is formed between —O— and a carbon atom in the Matrix, for removal of blood group A— and of blood group B-antibodies from blood or plasma.

25. The apparatus according to claim 1 wherein said apparatus contains bio-affinity material consisting of GalNAcα1-3(Fucα1-2)Galβ-O(CH$_2$)$_2$PhNH—CO—(CH$_2$)$_5$NH—CH$_2$—CH(OH)—CH$_2$—O-Matrix or of Galα1-3(Fucα1-2)Galβ-O(CH$_2$)$_2$PhNH—CO—(CH$_2$)$_5$NH—CH$_2$—CH(OH)—CH$_2$—O-Matrix for removal of blood group A— or of blood group B-antibodies, respectively, from blood or plasma.

26. The apparatus according to claim 1, wherein said apparatus contains bio-affinity material consisting of GalNAcα1-3(Fucα1-2)Galβ-O(CH$_2$)$_2$PhNH—CO—(CH$_2$)$_5$NH—CH$_2$—CH(OH)—CH$_2$—O-Matrix and of Galα1-3(Fucα1-2)Galβ-O(CH$_2$)$_2$PhNH—CO—(CH$_2$)$_5$NH—CH$_2$—CH(OH)—CH$_2$—O-Matrix for removal of blood group A— and of blood group B-antibodies from blood or plasma.

27. The apparatus according to claim 1, wherein said apparatus contains the Saccharide Galα1-3Galα-, Galα1-3Galβ-, Galα1-3Galβ1-4Glcβ-, Galα1-3Galβ1-4GlcNAcβ-, Galα1-3Galβ1-4GlcNAcβ1-3Galβ1-4Glcβ-, or of oligomeric ligands, selected from the group consisting of(Galα1-3Galα-)n-, (Galα1-3Galβ-)n-, (Galα1-3Galβ1-4Glcβ-)n-, (Galα1-3Galβ1-4GlcNAcβ-)n-, (Galα1-3Galβ1-4GlcNAcβ1-3Galβ1-4Glcβ-)n-, or (Galα1-3Galα- spacer)n-, (Galα1-3Galβ-spacer)n-, (Galα1-3Galβ1-4Glcβ-spacer)n-, (Galα1-3Galβ1-4GlcNAcβ-spacer)n-, and (Galα1-3Galβ1-4GlcNAcβ1-3Galβ1-4Glcβ-spacer)n-, where n is an integer larger than 1 for removal of antibodies directed towards said saccharides from blood or plasma.

28. An apparatus containing at least one biologically active saccharide covalently bound by at least one spacer to a cross linked matrix material, said apparatus being autoclavable and comprising:

a cylindrical container defined by a circumferential wall, having a top end and a bottom end, each of said top end and said bottom end having a protruding edge, a port defining an opening in said circumferential wall, said port protruding from the circumferential wall in an outward direction, a top lock cover in the form of a circular disk which has a downward projection to clip on to and under the protruding edge of said cylindrical container, said top lock cover being attachable to the top end of said container, said top lock cover having a central opening, a bottom lock cover in the form of a circular disk which has an upward projection to clip onto and over the protruding edge of said cylindrical container, said bottom lock cover being attachable to the bottom end of said container with said bottom lock cover having a central opening, said downward projection being of sufficient flexibility to engage with the protruding edge of said container and to permit said top lock cover to be pressed onto the container, optionally an outer ring located outside and adjacent to the top and bottom of the cylindrical housing to engage with and secure the top lock cover and bottom lock cover, respectively, a cover for said port, a first packing ring positioned between the upper end of said container and said top lock cover, a second packing ring positioned between the bottom end of said container and said bottom lock cover, said first and second packing ring each being fitted with a membrane located adjacent each of the top end and the bottom end of said container.

* * * * *

UNITED STATES PATENT AND TRADEMARK OFFICE
CERTIFICATE OF CORRECTION

PATENT NO. : 7,014,049 B2  Page 1 of 1
APPLICATION NO. : 10/114314
DATED : March 21, 2006
INVENTOR(S) : Kurt G. L. Nilsson It is certified that error appears in the above-identified patent and that said Letters Patent is hereby corrected as shown below:

Column 13, in Claim 19, line 33 the following phrase should be deleted "housing having"
Column 13, in Claim 20, line 42 the following phrase should be deleted "housing having"

Signed and Sealed this

Twenty-eighth Day of July, 2009

JOHN DOLL
*Acting Director of the United States Patent and Trademark Office*